United States Patent [19]

Hasegawa et al.

[11] Patent Number: 5,191,072
[45] Date of Patent: Mar. 2, 1993

[54] LIPID A MONOSACCHARIDE ANALOGUES

[75] Inventors: Akira Hasegawa; Makoto Kiso, both of Gifu; Shinichi Uesato, Yokohama; Masanobu Suzuki, Yokohama; Tomio Ishida, Yokohama; Yutaka Saito, Yokohama, all of Japan

[73] Assignees: Japan Tobacco Inc., Tokyo; Akira Hasegawa, Gifu, both of Japan

[21] Appl. No.: 689,770

[22] PCT Filed: Sep. 20, 1990

[86] PCT No.: PCT/JP90/01208
§ 371 Date: Jul. 17, 1991
§ 102(e) Date: Jul. 17, 1991

[87] PCT Pub. No.: WO91/04259
PCT Pub. Date: Apr. 4, 1991

[30] Foreign Application Priority Data

Sep. 20, 1989 [JP] Japan .................. 1-241866

[51] Int. Cl.$^5$ ............ C07H 11/00; C07H 13/00; C07H 13/02; A61K 31/70
[52] U.S. Cl. .................. 536/117; 536/119; 536/120; 536/115; 536/116; 536/17.9; 536/53; 514/23; 514/25; 514/42
[58] Field of Search .......... 536/117, 119, 120, 115, 536/116, 17.2, 17.9, 22; 514/23, 25, 42

[56] References Cited

U.S. PATENT DOCUMENTS 4,746,742  5/1988  Hasegawa et al. ............ 536/117

FOREIGN PATENT DOCUMENTS 60-501259  8/1985  Japan .
61-126093  6/1986  Japan .
61-126094  6/1986  Japan .
61-172867  8/1986  Japan .
61-246195  11/1986  Japan .
61-275299  12/1986  Japan .
62-108895  5/1987  Japan .
62-129292  6/1987  Japan .
63-30495  2/1988  Japan .
63-33391  2/1988  Japan .
63-44588  2/1988  Japan .
63-179885  7/1988  Japan .
64-52793  2/1989  Japan .
1-146892  6/1989  Japan .
2-25494  1/1990  Japan .
2-62888  3/1990  Japan .
2-62889  3/1990  Japan .

OTHER PUBLICATIONS

English abstract of Japanese Patent Application 61-275299.
English abstract of Japanese Patent Application 64-52793.
English abstract of Japanese Patent Application 63-179885.
English Abstract of Japanese Patent Application 2-62888.
English Abstract of Japanese Patent Application 61-126093.
English Abstract of Japanese Patent Application 61-126094.
English abstract of Japanese Patent Application 61-172867.
English abstract of Japanese Patent Application 62-129292.
English abstract of Japanese Patent Application 63-30495.
English abstract of Japanese Patent Application 2-25494.
English abstract of Japanese Patent Application 1-146892.
English abstract of Japanese Patent Application 63-44588.
English abstract of Japanese Patent Application 63-33391.
English abstract of Japanese Patent Application 2-62889.
Japanese Bacteriology Journal 40(1) 57 1985.
Proc. Natl. Acad. Sci., USA vol. 80, pp. 4624-4628, Aug. 1983.

Primary Examiner—Johnnie R. Brown
Assistant Examiner—Everett White
Attorney, Agent, or Firm—Birch, Stewart, Kolasch & Birch

[57] ABSTRACT

Lipid A monosaccharide analogues of the following general formula:

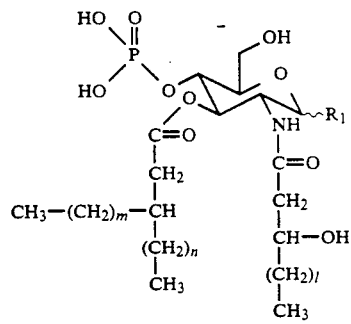

wherein $R_1$ is a hydrogen atom or a hydroxyl group, $l$ is an integer of 8-14, m is an integer of 11-17 integer, and n is 8-14 integer.

6 Claims, No Drawings

LIPID A MONOSACCHARIDE ANALOGUES

TECHNICAL FIELD

This invention relates to novel lipid A monosaccharide analogues which show lipid A-like activity and are useful as pharmaceutical drugs such as an immunopotentiator agent, and an anti-tumour agent.

BACKGROUND ART

Surface layers of Gram-negative bacteria are composed of cell membranes, cell wall peptide glucan surrounding the membrane, and outer membranes. The outer membrane contains lipopolysaccharide (hereinafter abbreviated LPS). LPS is a main ingredient of endotoxin which induces endotoxin shock, and consists of an acidic protein component, a high molecular polysaccharide component, and a phospholipid component.

LPS shows such functions as causing pyretogenesis, hemorrhage, arthritis, and encephalomyelitis. Moreover, LPS has been known to show immunopotentiating effect of a host-protecting mechanism such as macrophage activation, B cell blastogenesis, and cell-mediated immunity activation, as well as anti-tumor effect such as interferon induction, and TNF induction.

LPS expresses its activity mainly by the phospholipid part called lipid A among said three components. Lipid A comprises fatty acid residue and phosphoric acid both of which are combined with disaccharide amine, and has the following formula (Japanese Bacteriology Journal 40(1), 57(1985); Proc. Natl. Acad. Sci. USA. 80,4626 (1983)).

of the non-reducing subunit in lipid A into sulphuric acid residue.

Inventors of the present invention have made extensive investigation in order to synthesize lipid A derivatives which show a stronger immunomodulating activity. Specifically, by changing substituents or substituent-sites of a non-reducing subunit, many derivatives were synthesized. As a consequence, some of the derivatives synthesized as said have been found to show a strong immunopharmacological activity, and patent applications for them have already been filed (e.g., Japanese Patent Application Nos. 215613/88, 215612/88, and 172918/88, and Japanese Patent Disclosure Nos. 146892/89, 44588/88, 33391/88, 30495/88, 129292/87, 172867/86, 126094/86, and 126093/86).

As described above, extensive studies have been conducted in order to obtain lipid A analogues, specifically by modifying them with various substituents and by changing substituent sites introduced. However, such a problem has not yet overcome as obtaining different activities for different introduction sites of the same substituents, and thus lipid A analogues have not yet been developed which are applicable as pharmaceutical agents. Therefore compounds showing a more effective lipid A-like activity are earnestly expected to be developed.

SUMMARY OF THE INVENTION

An object of this invention is to provide novel lipid A monosaccharide analogues showing a strong immunomodulating activity analogous to lipid A.

The inventors of the present invention have energeti-

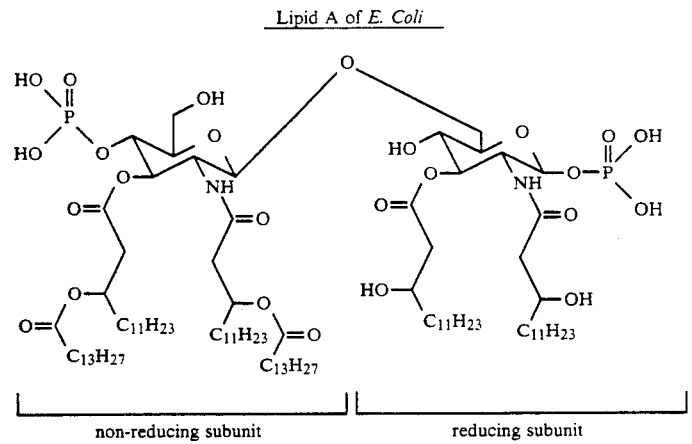

Lipid A of *E. Coli*

Recent study has revealed that either a nonreducing subunit or a reducing subunit as shown above alone is able to show lipid A-like activity. Based on this finding, various analogues have been synthesized concerning lipid A.

For example, Japanese Patent Disclosure No. 501259/85 discloses lipid A analogues which closely approximate to the reducing subunit and a method for producing the analogues. Japanese Patent Disclosure No. 146891/89 discloses monophosphoryl lipid A derivatives. Also, Japanese Patent Disclosure No. 246195/86 discloses novel disaccharide and trisaccharide derivatives of lipid A type. Japanese Patent Disclosure No. 275299/86 discloses deoxymuramyldipeptide derivatives. Further, Japanese Patent Disclosure Nos. 52793/89 and 179885/88 disclose glucopyranose derivatives obtained by converting a phosphoric acid residue cally studied in order to solve the problem stated above by finding a smaller structure and substituent introduction sites for expressing characteristic biological activity specific to lipid A. Consequently, we have found compounds which show strong activities, even though varying strengths, such as limulus activity, mitogenic activity, tumor necrosis factor inducing activity, and interferon inducing activity which resemble to those of natural lipid A, and completed this invention based on this finding.

Novel lipid A monosaccharide analogues according to this invention have the following formula [I]:

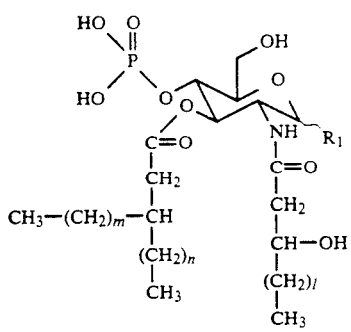

[I]

wherein $R_1$, l, m, and n in the formula indicate the followings respectively: $R_1$; a hydrogen atom or a hydroxyl group, l; 8–14 integer, m; 11–17 integer, and n; 8–14 integer.

DETAILED DESCRIPTION OF THE INVENTION

Lipid A monosaccharide analogues [I] of the present invention have a distinctive construction obtained by acylating the 3-position of pyranose ring with β-alkyl substituted fatty acid. Specifically, an analogue whose $R_1$ at the 1-position is a hydrogen atom shows a strong immunopharmacological activity, and thus its pharmaceutical use is highly expected.

The compound [I] includes various stereoisomers. Both of isolated stereoisomers and a mixture of them are included in this invention.

These lipid A monosaccharide analogues [I] can be produced e.g. by a reaction shown in the following flow 1.

Flow-1

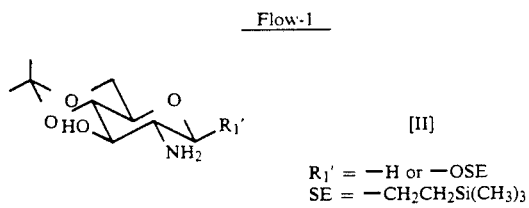

[II]

$R_1' = -H$ or $-OSE$
$SE = -CH_2CH_2Si(CH_3)_3$ (the first step) ↓

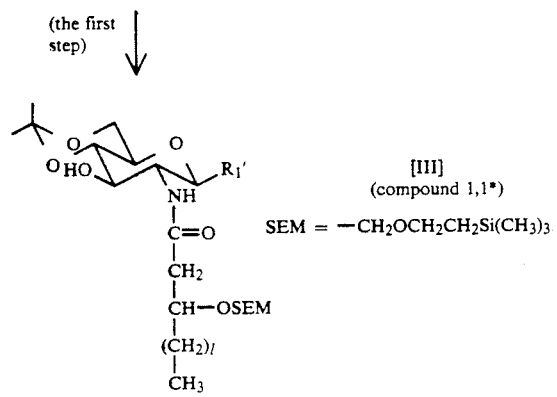

[III] (compound 1,1*)

$SEM = -CH_2OCH_2CH_2Si(CH_3)_3$ (the second step) ↓

-continued
Flow-1

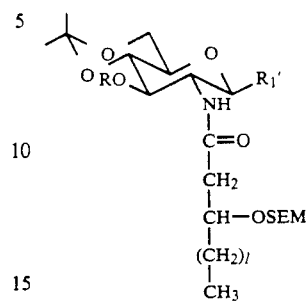

[IV] (compound 2~9,7*)

(the third step) ↓ $R = -\overset{O}{\underset{}{C}}-CH_2-\underset{(CH_2)_m-CH_3}{\overset{|}{CH}}-(CH_2)_n-CH_3$

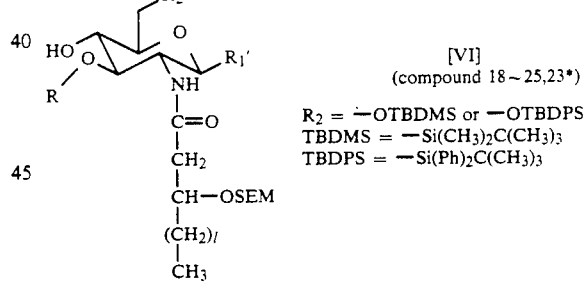

[V] (compound 10~17,15*)

(the fourth step) ↓

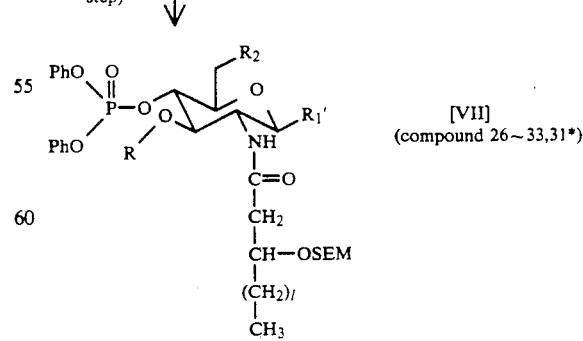

[VI] (compound 18~25,23*)

$R_2 = -OTBDMS$ or $-OTBDPS$
$TBDMS = -Si(CH_3)_2C(CH_3)_3$
$TBDPS = -Si(Ph)_2C(CH_3)_3$ (the fifth step) ↓

[VII] (compound 26~33,31*)

(the sixth step) ↓

-continued
Flow-1

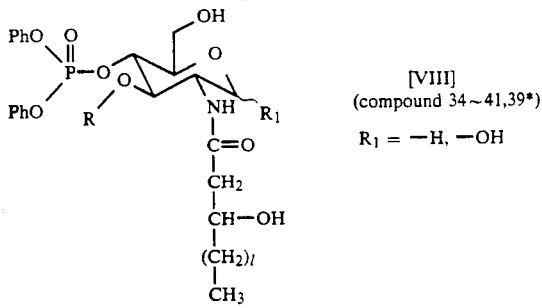

[VIII]
(compound 34~41,39*)

$R_1 = -H, -OH$ (the seventh step) ↓

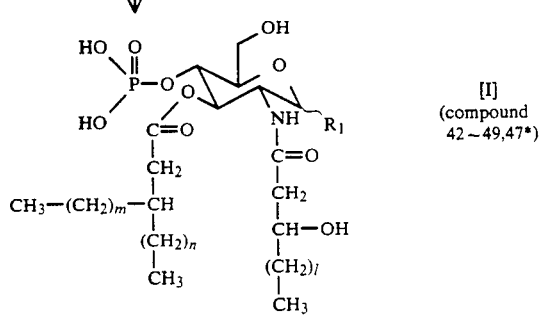

[I]
(compound 42~49,47*)

Each step of said flow 1 is described in detail as follows.

First Step

The known compound [II] derived from D-glucosamine or 1,5-anhydro-glucitol (e.g. See Japanese Patent Disclosure No. 197582/86) is amidated with a fatty acid compound comprising a 2-(trimethylsilyl)ethoxymethoxy group at the 3-position to yield a compound [III].

Second Step

The glucosamine derivatives [III] such as 2-(trimethylsilyl)ethyl 2-deoxy-4,6-0-isopropyriden-2-{(3R)-3-[2-(trimethylsilyl)ethoxymethoxy]-tetradecanamido}-β-D-glucopyranoside, whose hydroxyl groups other than that at 3-position are suitably protected are acylated with β-alkyl subsutituted fatty acid (ROH) to give a compound [IV]. This reaction is conducted in a solution such as dischloromethane containing a catalytic amount of dimethylaminopyridine in the presence of 1-ethyl-3-(3-dimethylaminopropyl)carbodiimide hydrochloride.

Third Step

The compound [IV] obtained in the second step is hydrolyzed with an aqueous acetic acid in order to eliminate protecting groups at 4,6-positions. A compound [V] is thus obtained.

Fourth Step

The compound [V] is treated with tert-butyldimethylsilyl chloride or tert-butyldiphenylsilyl chloride in a solvent such as dimethylformamide and pyridine, in the presence of imidazole as needed, in order to protect a hydroxyl group at 6-position. A compound [VI] is thus obtained.

Fifth Step

The compound [VI] is dissolved in a solvent such as pyridine, together with dimethylaminopyridine (DMAP). To this solution, diphenyl phosphorochloridate dissolved in dichloromethane, etc. is added. By this reaction, a compound [VII] is obtained which has a diphenylphosphoryl group at 4-position.

Sixth Step

BF$_3$.OEt$_2$ is added to a solution of the compound [VII] in a solvent such as dichloromethane. By this reaction, protective groups at 6-position of the ring, at 3-position of tetradecanamide residue which is bonded to 2-position of the ring, and at 1-position of the pyranose ring as needed are eliminated to yield a compound [VIII].

Seventh Step

The compound [VIII] is hydrogenated over PtO$_2$, etc. in a solvent such as ethanol to afford an objective compound [I] possessing a phosphoryl group at the 4-position.

When a compound [I] whose R$_1$ is a hydroxyl group is desired, this hydroxy group should be protected with a SE group during the steps 1-5.

β-Alkyl substituted fatty acid (vi) utilized in the second step can be produced, for example, according to the following flow 2.

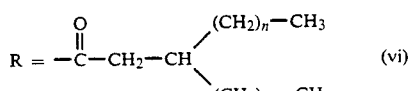

Flow-2

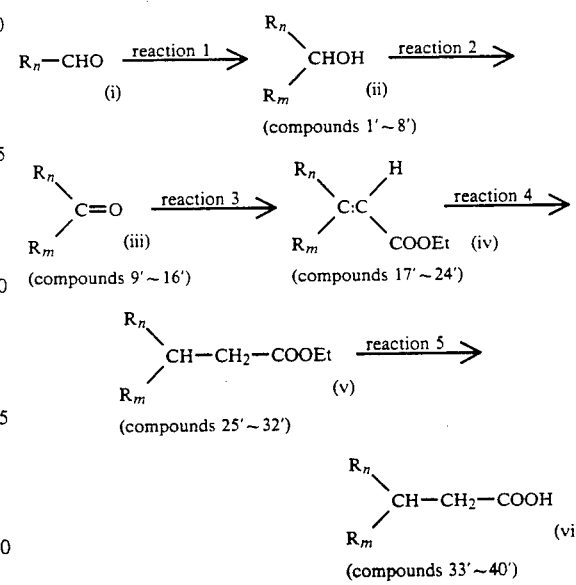

wherein R$_n$ indicates H$_3$C(CH$_2$)$_n$-, and R$_m$ indicates H$_3$C(CH$_2$)$_m$-.

Each step of the flow 2 is as follows:

Reaction 1

1-Halogenated alkyl is reacted with metal magnesium in an anhydrous solvent to prepare Grignard reagent of H$_3$C—(CH$_2$)mMgBr type. This Grignard reagent is reacted with aldehyde of the formula (i) to obtain a secondary alcohol of the formula (ii).

Reaction 2

The compound (ii) is oxidized in dried dichloromethane to obtain a ketocompound (iii). An oxidizing reagent used here is PCC (pyridinium chlorochlomate).

Reaction 3

This reaction is called Wittig reaction. Sodium hydride and then the compound (iii) are added to dried benzene containing triethyl phosphonoacetate to yield a compound (iv).

Reaction 4

The compound (iv) is hydrogenated in the presence of catalyst such as palladium carbon in a solvent to give an ester compound (v).

Reaction 5

The compound (v) is hydrolyzed with alkali, etc. to furnish the objective compound, β-alkyl substituted fatty acid (vi).

Compound Nos. of β-alkyl substituted fatty acid obtained in the flow 2 and their intermediates, and relations between these compounds and their chemical constructions are shown in Table 1.

Also, compound Nos. of β-alkyl substituted fatty acid used in said flow 1, lipid A monosaccharide analogues obtained in the flow 1, and their intermediates and relations between these compounds and their chemical constructions are shown in Table 2.

TABLE 1

β-alkyl substituted fatty acid and its intermediates (reactions 1 to 5)

$H_3C-(CH_2)_n$
$\phantom{H_3C-(CH_2)_n}\diagdown$
$\phantom{H_3C-(CH_2)_n\diagdown}C$ compounds (ii) to (vi) and
$\phantom{H_3C-(CH_2)_n\diagup}\diagup\phantom{C}\diagdown$ their compound numbers
$H_3C-(CH_2)_m$

| n | m | (ii) | (iii) | (iv) | (v) | (vi) |
|---|---|---|---|---|---|---|
| 8 | 11 | 1' | 9' | 17' | 25' | 33' |
| 8 | 13 | 2' | 10' | 18' | 26' | 34' |
| 8 | 15 | 3' | 11' | 19' | 27' | 35' |
| 8 | 17 | 4' | 12' | 20' | 28' | 36' |
| 10 | 11 | 5' | 13' | 21' | 29' | 37' |
| 10 | 13 | 6' | 14' | 22' | 30' | 38' |
| 10 | 15 | 7' | 15' | 23' | 31' | 39' |
| 10 | 17 | 8' | 16' | 24' | 32' | 40' |

TABLE 2

Lipid A monosaccharide analogues and their intermediates (the second step ~ the seventh step)

$R = -\overset{O}{\underset{\|}{C}}-CH_2CH\diagupdiagdown\overset{(CH_2)_n-CH_3}{\underset{(CH_2)_m-CH_3}{}}$ Compounds [IV] to [VIII] and [I], and their compound numbers (wherein, l = 10, $R_1' = -OSE$, $R_1 = -OH$, $R_2 = -OTBDMS$ or $-OTBDPS$)

| n | m | [IV] | [V] | [VI] | [VII] | [VIII] | [I] |
|---|---|---|---|---|---|---|---|
| 8 | 11 | 2 | 10 | 18 | 26 | 34 | 42 |
| 8 | 13 | 3 | 11 | 19 | 27 | 35 | 43 |
| 8 | 15 | 4 | 12 | 20 | 28 | 36 | 44 |
| 8 | 17 | 5 | 13 | 21 | 29 | 37 | 45 |
| 10 | 11 | 6 | 14 | 22 | 30 | 38 | 46 |
| 10 | 13 | 7 | 15 | 23 | 31 | 39 | 47 |
| 10 | 15 | 8 | 16 | 24 | 32 | 40 | 48 |
| 10 | 17 | 9 | 17 | 25 | 33 | 41 | 49 |
| 10 | 13 | 7* | 15* | 23* | 31* | 39* | 47* |

(For compound with * marks, l = 10, $R_1 = R_1' = -H$, $R_2 = OTBDPS$)

Next, use of compounds in this invention as pharmaceutical drugs is described.

The compound of the general formula [I] is generally administered systemically or topically, and orally or parenterally.

Although administered dose varies with age, weight, and symptom of a patient in question, therapeutic effect desired, administration route, treatment period, etc., 0.01–100 mg of the compound is generally administered orally or parenterally to an adult once to several times a day.

Solid compositions prepared to be orally administered according to this invention include tablets, powder, granules, etc.. These solid compositions are obtained by mixing at least one active substance with at least one inert diluent or dispersing agent. Examples of the diluents or dispersing agents include lactose, mannitol, glucose, hydroxypropylcellulose, crystalline cellulose, starch, polyvinylpyrrolidon, magnesium aluminometasilicate, etc.. Other than these diluents or dispersing agents, adsorbents such as anhydrous silica powder, etc. may be mixed with the compound [I]. Further, the solid compositions may contain additives other than inactive diluents, according to a general method.

The tablets or pills stated above may be coated, if desired, with acid soluble films or enteric coating films such as saccharose, gelatin, hydroxypropylcellulose and hydroxypropylmethylcellulose phthalate. Some tablets or pills may be coated, if desired, with two or more these films. Also powder or granules may be encapsulated within capsules made of gelatin, ethylcellulose, etc..

Examples of liquid compositions for oral administration include pharmaceutically acceptable emulsion, solution, suspension, syrup, erixil, etc. These liquid compositions may contain inert diluents generally utilized, e.g., purified water, ethanol, vegitable oils, emulsifying agent. Further, auxiliary agents such as moisturing agents or suspending agents, edulcorants, flavouring agents, perfumes, and antiseptics may be contained in the compositions.

Injectable preparations for parenteral administration may contain sterilized aqueous or non-aqueous solvents, solubilizing agents, suspending agents, and emulsifying agents. Examples of the aqueous solvents, solubilizing agents, and suspending agents include distilled water for injection, saline solution, cyclodextrin and its derivatives, organic amines such as triethanolamine, diethanolamine, monoethanolamine, and triethylamine, and inorganic alkalines.

Examples of the non-aqueous solvent include propyleneglycol, polyethyleneglycol, vegitable oils such as olive oil, and alcohols such as ethanol. Examples of non-aqueous solubilizing agents include surfactants (which forms mixed miscells) such as polyoxyethylene hydrogenated castor oil, and sucrose fatty acid ester, lecithin, and hydrogenated lecithin (which forms liposomes), etc. Emulsion preparations are also included in the non-aqueous solution preparation, which are obtained by using non-aqueous solvent such as vegitable oils with emulsifying agents such as lecithin, polyoxyethylene hydrogenated castor oils, and polyoxyethylenepolyoxypropyleneglycol.

Examples of other compositions which are administered via any route other than per os are topical solutions, liniments such as ointments, suppositories, pessaries, etc., each of which contains at least one active substance and is prepared according to the disclosed method.

Hereinafter are described pharmacological actions of the compounds according to this invention by way of experimental examples. The compounds according to this invention have showed significant effects for various tests such as IL-1-producing activity, and mitogenic activity, colony stimulating factor-inducing activity, and also showed low toxicities for tests such as local Schwartzman reaction, and pyrogenicity. Some activities are stated as follows.

EXPERIMENTAL EXAMPLE 1

$O_2^-$ Production Stimulating Activity in Neutrophils $O_2^-$ production stimulating activity in neutrophils was evaluated utilizing the following experimental system [see J. Exp. Med., 160, 1656-1671, 1984]. To the peritoneal cavity of $C_3H/HeN$ mouse (male, 8-9 week-aged), physiological saline containing 0.2% (w/v) casein was administered. Three hours later, peritoneal exudate cells (90% or more of which are neutrophils) were collected. These cells ($1.7 \times 10^6$ cells/ml/tube) were incubated in the presence of the compound according to this invention (1 μg/ml) at 37° C. for 60 minutes. After addition of 80 μM of cytochrome C and 0.1 μM of formyl-methionyl-leucyl-phenylalanine (FMLP), the mixture was incubated in the presence of or in the absence of Superoxide dismutase (SOD) at 37° C. for 10 minutes. Then, SOD-inhibitable cytochrome C reduction was estimated from the difference between absorbances at 550 nm and 541.7 nm, and from molar absorption coefficient ($16.5 \times 10^3$). $O_2^-$ production-stimulating activity was shown in Stimulation % in the following formula.

Stimulation % = (the amount of $O_2^-$ produced in the presence of compounds of the invention)/(the amount of $O_2^-$ produced in the absence of compounds of the invention) × 100 − 100

The compounds of this invention revealed the following activities as shown in the following Table.

GLA60 in this Table is 2-deoxy-2-(3-hydroxytetradecanaymidno)-4-0-phosphorno-3-0-[(3-O-tetradecanoyl)-tetradecanoyl]-D-glucopyranose, and is said to be relatively high in its activity among known lipid A monosaccharide analogues.

TABLE

| Compounds | Stimulation % |
|---|---|
| No compounds of this invention | 0 |
| GLA60 | 71 |
| Compound 47* | 111 |
| Compound 47 | 73 |
| Compound 48 | 69 |

EXPERIMENTAL EXAMPLE 2

TNF-Producing Activity

TNF-producing activity was evaluated utilizing the following experiment system.

The first stimulating agent, 5% Corynebacterium parvum suspension (0.2 ml physiological saline solution) was intravenously administered to ICR mouse (female, 6-7 week-aged). Nine days later, the second stimulating agent, the compound of this invention was intravenously administered to the same mouse at 10 μg/mouse. In 90 minutes, 0.5-1 ml of blood was taken from the retro orbital plexus. The obtained blood was allowed to clot at room temperature for five to six hours, and centrifuged at 7200×g for five minutes to separate serum. The obtained serum was incubated at 56° C. for 30 minutes for inactivation before use in the following experiment.

TNF activity in the serum was measured with cytotoxicity assay using L929 cells. L929 cells were prepared in concentration of $6 \times 10^4$ cells/well (0.1 ml) RPMI 1640 medium containing 10% FBS and 2 μg/ml actinomycin D in 96-well plates. Serial dilution of obtained serum in RPMI 1640 medium containing 10% FBS was added to each well in the plate (0.1 ml/well). After a 48 hr incubation at 37° C., the viable cells were fixed with methanol. These cells were then stained with 0.2% crystal violet, and the dye was extracted with 1% SDS. Next, absorbance at 550 nm was measured. Finally, cytotoxicity ratio (%) was calculated according to the following formula, and the reciprocal of dilution of the serum showing 50% cytotoxicity was determined for TNF titer in serum (U/ml).

Cytotoxicity (%) = [$OD_{550}$ (medium alone) − $OD_{550}$ (serum obtained by administering compounds of the invention)] × 100/$OD_{550}$ (medium alone)

The compounds of this invention revealed activities shown in the following Table.

TABLE

| compound | the amount of the TNF in serum (U/ml) |
|---|---|
| No compounds of this invention | <10 |
| GLA 60 | 216809 |
| compound 47* | 251308 |
| compound 46 | 292354 |
| compound 47 | 235919 |

EXPERIMENTAL EXAMPLE 3

Lethal Toxicity in Galactosamine-Sensitized Mice

Lethal toxicity in galactosamin-sensitized mice was evaluated by utilizing the following experiment system [see J.Biochem., 98, 395-406 pp., 1985].

To C57BL mouse (male, 7-week aged), 10 mg/mouse of D-galactosamine/HCl was intraperitoneally administered. Immediately after that, the compound of this invention was intravenously administered. After these administrations, general conditions of the mouse were observed every one hour for seven hours, and every day from the following day to the seventh day.

The compound of this invention showed lethal toxicity as in the following table;

TABLE

| Compound | $LD_{50}$ (galactosamine load) (μg/kg) |
|---|---|
| Lipid A | 0.3 |
| GLA60 | 3.0 |
| Compound 47* | 11.8 |

EXPERIMENTAL EXAMPLE 4

Nonspecific Protective Activity Against Bacterial Infection in Immunosuppressed Mouse Protective effect against bacterial infection in immunosuppressed mouse was evaluated by utilizing the following experiment system.

To a group of ten ICR mice (male, 5-week aged), cyclophosphamide (200 mg/kg) was intraperitoneally administered. Three days later, the compound of this invention was also intraperitoneally administered. Twenty four hours later, E.coli. 589 strain, was intraperitoneally inoculated at $1.0 \times 10^7$ CFU/mouse. The protective activities against infection was evaluated from survival rate (%) of mice after six days of bacterial infection.

Consequently, the compound of this invention showed the autimicrobial activities as in the following table.

TABLE

|  | survival rate of mice after six days of infection |
|---|---|
| No compounds of this invention | 28 |
| Lipid A |  |
| (0.05 mg/kg) | 75 |
| GLA 60 |  |
| (0.005 mg/kg) | 33 |
| (0.05 mg/kg) | 43 |
| (0.5 mg/kg) | 70 |
| compound 47* |  |
| (0.005 mg/kg) | 46 |
| (0.05 mg/kg) | 63 |
| (0.5 mg/kg) | 80 |

Best Mode of Carrying Out the Invention

The following is the detailed descriptions of this invention by way of concrete examples of methods for producing the compound [I].

First, a method for producing β-alkyl substituted fatty acid used for producing the compound [I] is described in a production example I. A method for producing intermediate products [III]–[VIII] for a final objective compound [I] is described in a production example II. Finally, a method for producing the objective compound [I] is described according to an embodiment. However, it should be noted that this invention is not restricted to the examples.

PRODUCTION EXAMPLE I: PRODUCTION OF β-ALKYL SUBSTITUTED FATTY ACID (SEE THE FLOW 2)

Production Example I-1 (Reaction 1; Production of the Compound (ii))

(RS)-12-hexacosanol (compound 6')

Magnesium (0.24 g), and catalytic amounts of iodine and dibromoethane were suspended in dried tetrahydrofuran (5 ml) under an argon atmosphere. To the resultant solution was dropwise added a dried tetrahydrofuran solution (10 ml) containing 2.77 g of 1-bromotetradecane.

One hour later, 5 ml of dried tetrahydrofuran solution containing 1.84 g of n-dodecyl aldehyde was dropped into the mixture obtained above, followed by stirring at room temperature overnight. The reacted solution was poured into a diluted hydrochloride solution and extracted with ether. The ether layer was washed successively with water, sodium bicarbonate solution and saturated saline solution, and dried with anhydrous $MgSO_4$. After evaporation of ether, the residue was recrystallized from n-hexane to obtain a clourless crystal (the compound 6') (2.67 g, yield: 70%). Physical data of this product were as follows:

mp: 75°–77.5° C.

$^1$H-NMR (90 MHz, $CDCl_3$) δ: 0.88 (t, 6H, J = 6.2 Hz, —Me), 1.0–1.7 (m, 46H, —$CH_2$—), 1.80 (brs, 1H, —OH), 3.60 (m, H, —CH—O)

Further, the compounds 1', 2', 3', 4', 5', 7', and 8' of the general formula (ii) were obtained in the same manner:

| compounds | $R_n$ | $R_m$ | melting point (°C.) |
|---|---|---|---|
| 1' | $CH_3(CH_2)_8$— | $CH_3(CH_2)_{11}$— | 64–65 |
| 2' |  | $CH_3(CH_2)_{13}$— | 67.5–68.5 |
| 3' |  | $CH_3(CH_2)_{15}$— | 70.5–72.5 |
| 4' |  | $CH_3(CH_2)_{17}$— | 75–77 |
| 5' | $CH_3(CH_2)_{10}$— | $CH_3(CH_2)_{11}$— | 75–76 |
| 6' |  | $CH_3(CH_2)_{13}$— | 75–77.5 |
| 7' |  | $CH_3(CH_2)_{15}$— | 76–77 |
| 8' |  | $CH_3(CH_2)_{17}$— | 76.5–78.5 |

Production Example I-2 (Reaction 2; Production of the Compound (iii))

12-hexacosanone (compound 14')

The compound 6' (1.0 g) and PCC (pyridinium chlorochlomate, 1.1 g) were suspended in dried dichloromethane (30 ml), and the mixture was stirred overnight. Next, the reaction mixture was transferred to a Florisil column, eluted with ether, and the obtained eluate was concentrated. The resultant residue was recrystallized from petroleum ether to give a colorless crystal (the compound 14') (0.94 g, yield: 95%). Physical data of this product were as follows:

mp: 67°–68° C.

$^1$H-NMR (90 MHz, $CDCl_3$) δ: 0.88 (t, 6H, J=6.2 Hz, —Me), 1.10–1.85 (m, 42H, —$CH_2$—), 2.38 (t, 4H, J=7.5 Hz, —$CH_2$—CO—)

By utilizing the same method, the compounds 9', 10', 11', 12', 13', 15', and 16' of the following general formulas were prepared.

$$\begin{matrix}R_n\\R_m\end{matrix}\!\!\!\!\Bigg\rangle=O$$

| compounds | $R_n$ | $R_m$ | melting point (°C.) |
|---|---|---|---|
| 9' | $CH_3(CH_2)_8$— | $CH_3(CH_2)_{11}$— | 57.5–58 |
| 10' |  | $CH_3(CH_2)_{13}$— | 62.5–63 |
| 11' |  | $CH_3(CH_2)_{15}$— | 68.5–70.5 |
| 12' |  | $CH_3(CH_2)_{17}$— | 72–73 |
| 13' | $CH_3(CH_2)_{10}$— | $CH_3(CH_2)_{11}$— | 64–66 |
| 14' |  | $CH_3(CH_2)_{13}$— | 67–68 |
| 15' |  | $CH_3(CH_2)_{15}$— | 71–72 |
| 16' |  | $CH_3(CH_2)_{17}$— | 75–76 |

Production Example I-3 (Reaction 3; Production of the Compound (iv))

Compound 22'

(E, Z)-ethyl 3-undecyl-2-heptadecanoate

To dried benzene (5 ml) containing triethylphosphonoacetate (900 mg), sodium hydride (60% suspension in mineral oil) (195 mg) was added under an argon atmosphere, followed by stirring for 30 minutes. Then the compound 14' (760 mg) was added and the mixture was further stirred with heating at 80° C. for 10 hours. The reaction solution was diluted with ether, washed with water, dried with anhydrous MgSO₄ and concentrated. The residue was purified by a silica gel column (n-hexan/ethyl acetate=10/1) to yield an oily substance (the compound 22') (751 mg, yield: 83%). Physical data of this product were as follows:

¹H—NMR (300 MHz, CDCl₃) δ: 0.88 (t, 6H, J=6.4 Hz, —Me), 1.15-1.52 (m, 45H, —CH₂— and —CH₃), 2.12 (t, 2H, J=7.0 Hz, —CH₂—C≡C) 2.58 (t, 2H, J=8.2 Hz, —CH₂—C≡C), 4.13 (q, 2H, —OCH₂), 5.60 (s, 1H, HC=C—)

MS: 451/450 (M⁺+1/M⁺)

Calcd. C₃₀H₅₈O₂=450.8

In the same manner as described above, compounds 17', 18', 19', 20', 21', 23', and 24' of the following general formula were prepared.

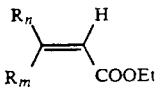

The ¹H—NMR of these compounds were the same as that of the compound 22' except for an integrated value of a CH₂ region.

Production Example I-4 (Reaction 4; Production of the Compound (v))

compound 30'

(RS)—ethyl 3-undecylheptanoate

The compound 22' (700 mg) was hydrogenated in the presence of 5% palladium carbon (70 mg) was added, followed by hydrogen addition. One hour later, the catalyst used was removed by filtration, and the filtered solution was concentrated to obtain an oily substance (compound 30') (700 mg, quant.). Physical data of this product were as follows:

¹H—NMR (300 MHz, CDCl₃) δ: 0.88 (t, 6H, J=6.2 Hz, —Me), 1.15-1.50 (m, 49H, —CH₂— and —Me), 1.84 (m, 1H, —CH—), 2.21 (d, 2H, J=6.9 Hz, —CH₂—CO—), 4.12 (q, 2H, J=7.1 Hz, —OCH₂—)

MS: 452 (M⁺)

Calcd. C₃₀H₆₀O₂=452.8

In the same manner as mentioned above, the compounds 25', 26', 27', 28', 29', 31', and 32' of the following general formula were prepared:

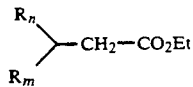

The ¹H—NMR of these compounds were the same as that of the compound 30' except for an integrated value of a CH₂ region.

Production Example I-5 (Reaction 5; Production of the Compound (vi))

compound 38'

(RS)-3-undecylheptadecanoic acid

The compound 30' (452 mg) was dissolved in a solution (ethylalcohol/water=10/1)(10 ml) containing 5% potassium hydroxide, and the mixture was refluxed with heating for three hours. The solution was diluted with water, acidified with diluted hydrochloric acid solution, and extracted with ether. After the ether layer was concentrated, the resultant residue was purified with a silica gel column (CHCl₃) to obtain a colourless crystal (compound 38') (340 mg, yield: 80%). Physical data of this product were as follows:

mp: 43.5°-45 ° C.

IR (KBr)cm⁻¹; 3500-2400, 1710, 1290

¹H—NMR (300 MHz, CDCl₃) δ: 0.88 (t, 6H, J=6.3 Hz, —Me), 1.10-1.57 (m, 46H, —CH₂—), 1.85 (m, 1H, —CH<), 2.27 (d, 2H, J=6.8 Hz)

Further, the compounds 33', 34', 35', 36', 37', 39', and 40' of the following general formula were obtained in the same way as mentioned above:

$$\begin{array}{c} R_n \\ \phantom{R_n}\diagdown \\ \phantom{R_nR}\diagup\!\!\!\!\text{CH}_2\text{—CO}_2\text{H} \\ R_m \end{array}$$

| compounds | $R_n$ | $R_m$ | melting point (°C.) |
|---|---|---|---|
| 33' | CH₃(CH₂)₈— | CH₃(CH₂)₁₁— | 31-31.5 |
| 34' | | CH₃(CH₂)₁₃— | 32-32.5 |
| 35' | | CH₃(CH₂)₁₅— | 37-38 |
| 36' | | CH₃(CH₂)₁₇— | 50.5-51 |
| 37' | CH₃(CH₂)₁₀— | CH₃(CH₂)₁₁— | 35.5-36 |
| 38' | | CH₃(CH₂)₁₃— | 43.5-45 |
| 39' | | CH₃(CH₂)₁₅— | 45.5-47 |
| 40' | | CH₃(CH₂)₁₇— | 49-51 |

PRODUCTION EXAMPLE II: A METHOD FOR PRODUCING INTERMEDIATES [III]-[VIII] (SEE THE FLOW 1)

Production Example II-1 (The First Step; Production of the Compound [III])

compound 1* (R₁'=—H)

1,5-anhydro-2-deoxy-4,6-O-isopropyriden-2-{(3R)-3-[2-(trimethylsilyl) ethoxymethoxy]-tetradecanamido}-D-glucitol 2-Amino-1,5-anhydro-2-deoxy-4,6-0-isopropyriden-D-glucitol (5.8 g) (Japanese Patent Disclosure No. 197582/86) derived from D-glucosamine, (R)-3-[2-(trimethylsilyl)ethoxymethoxy]tetrdecanoic acid (10.7 g) (a known substance) derived from (R)-3-hydroxytetradecannoic acid, and 1-ethyl-3-(3-dimethylaminopropyl)-carobodiimide hydrochloride (11 g) (hereinafter called WSC) were dissolved into dried dichloromethane (44 ml), and the resultant solution was stirred under ice-cooling. During stirring, reaction was monitored utilizing a thin layer chromatography (silica gel, CHCl₃/MeOH=20/1). After the reaction went to completion, the mixture was diluted with dichloromethane, washed with water, and dried with anhydrous MgSO₄. The solvent was removed under a reduced pressure, and the resultant residue was purified with a silica gel column (CHCl₃/MeOH=100/1) to yield a colourless crystal (the compound 1*, R1'=-H) (14 g, yield: 88%). Physical data of this product were as follows:

[α]_D: —6.90° (C=1.10, CH₂Cl₂)

mp: 61°-62° C.

IR(nujol)cm⁻¹: 3450, 3280, 1640, 1550, 1460, 1380, 860-830

¹H—NMR (300 MHz, CDCl₃) δ: 0.03 (s, 9H, Me₃Si), 0.85-0.97 (m, 5H, TMSCH₂, —Me), 1.2-1.6 (m, 20H,

—CH$_2$—), 1.43, 1.52 (each s, 6H, —CMe$_2$—), 2.38, 2.48 (AB part of ABX, 2H, J$_{AB}$=14.9, J$_{AX}$=6.6, J$_{BX}$=4.0 HZ, —CH$_2$—CO—) 3.22 (m, 2H, H-1, H-5), 3.44 (brs, 1H, —OH), 3,54-3.65 (m, 4H, H-1, H-4, O—CH$_2$CH$_2$—TMS) 3.72 (t, 1H, J=10.5 Hz, H-6), 3.87-3.92 (m, 2H, H-6, CH-OSEM), 4.01-4.09 (m, 2H, H-2, H-3) 4.67, 4.75 (AB, 2H, J$_{AB}$=6.6 Hz, —OCH$_2$O—) 6.47 (d, 1H, J=7.0 Hz, NH)

The compound 1 included in the general formula [III] having OSE as R$_1'$ can also be produced in the same manner as said.

Production Example II-2 (The Second Step; Production of the Compound [IV])

compound 7*

1,5-Anhydro-2-deoxy-4,6-O-isopropyriden-2-{(3R)-3-[2-(trimethylsilyl)ethoxymethoxy]tetradecanamido}-3-O-[(3RS)-3-undecylheptadecanoyl]-D-glucitol The compound 1 (3 g), (RS)-3-undecylheptadecanoic acid (the compound 38') (2 g), WSC (2.04 g), and dimethylaminopyridine (hereinafter abbreviated DMAP) (0.1 g) were dissolved into dried dichloromethane, and the solution was stirred for 3 hours at the room temperature. The mixture was diluted with dichloromethane, washed with water, dried with anhydrous MgSO$_4$, and concentrated under a reduced pressure. The residue was purified with a silica gel column (CH$_2$Cl$_2$/MeOH=100/1-50/1) to obtain an amorphous compound 7* (4.12 g, yield: 91%). Physical data of this product were as follows:

IR (film)cm-$^1$: 3320, 2900, 1735, 1645, 1545, 1470, 1383

$^1$H—NMR (300 MHz, CDCl$_3$) δ: 0.03 (s, 9H, Me$_3$Si), 0.86-0.97 (m, 11H, TMSCH$_2$, —Me), 1.18-1.60 (m, 66H, —OCH$_2$—), 1.36, 1.47 (each s, 6H, —CMe$_2$), 1.85 (m, 1H, —CH<), 2.2-2.4 (m, 4H, —CH$_2$CO—), 3.1-4.0 (m, 8H, H$_2$-1, H-4, H-5, H$_2$-6, —O—CH$_2$CH$_2$ TMS), 4.16 (m, 2H, H-2, CH-OSEM), 4.66, 4.68 (AB, 2H, J$_{AB}$=6.9 Hz, —OCH$_2$O—), 4.94 (t, 1H, J=9.6 Hz, H-3), 6.27 (d, 1H, J=7.0 Hz, NH)

compound 2

2-(trimethylsilyl)ethyl 2-deoxy-4,6-O-isopropyriden-3-O-[(3RS)-3-nonylpentadecanoyl]-2-{(3R)-3-[2-(trimethylsilyl) ethoxymethoxy]tetradecanamido}-β-D-glucopyranoside 2-(Trimethylsilyl)ethyl 2-deoxy-4,6-O-isopropyriden-2-{(3R)-3-[2-(trimethylsilyl)ethoxymethoxy]tetradecanamido}-β-D-glucopyranoside (the compound 1, R$_1$=—OSE) (400 mg) was dissolved in dichloromethane. To the obtained solution, (RS)-3-nonylpentadecanoic acid (the compound 33') (469 mg), WSC (339 mg) and a catalytic amount of DMAP were added, and the mixture was stirred at room temperature overnight. The resultant solution was directly subjected to a column chromatography (Wakogel C-200). Elution with CH$_2$Cl$_2$/MeOH=300/1 afforded a syrupy compound 2 (620 mg). Physical data of this product were as follows:

[α]$_D$: −12.8° (C=0.97, CH$_2$Cl$_2$)

IR (film)cm-$^1$: 3300, 2930, 2860, 1740, 1650, 1550, 860, 830

$^1$H—NMR (270 MHz, CDCl$_3$) δ: 0.0 (m, 18H, Me$_3$Si), 0.8-1.0 (m, 13H, Me$_3$SiCH$_2$— and —Me), 1.1-1.65 (m, 59H, —CH$_2$—, —CH—), 1.32, 1.42 (2s, 6H, Me$_2$C), 2.1-2.4 (m, 4H, —COCH$_2$—), 3.34 (m, 1H, H-5), 3.4-4.0 (m, 9H, TMSCH$_2$ C$\underline{H}_2$, H-3 of C$_{14}$-OSEM, H-2, 4, 6), 4.51 (d, 1H, J=8.1 Hz, H-1), 4.62, 4.69 (2d, 2H, J=7.0 Hz, —OCH$_2$O—), 5.11 (t, 1H, J=9.5 Hz, H-3), 6.20 (d, 1H, J=9.5 Hz, NH)

Compound 3

2-(trimethylsilyl)ethyl 2-deoxy-4,6-O-isopropyriden-3-O-[(3RS)-3-nonylheptadecanoyl]-2-{(3R)-3-[2-(trimethylsilyl)ethoxymethoxy]tetradecanamido}-β-D-glucopyranoside The compound 1 (400 mg) was reacted with (RS)-3-nonylheptadecanoic acid (the compound 34') (502 mg) in the same manner as that for the compound 2 to yield a syrupy compound 3 (600 mg, yield: 94%). Physical data of this product were as follows:

[α]$_D$: −12.2° (C=0.98, CH$_2$Cl$_2$)

IR: the same as for the compound 2

$^1$H—NMR: the same as for the compound 2 except for a —CH$_2$— integration value Compound 4

2-(trimethylsilyl)ethyl 2-deoxy-4,6-O-isopropyriden-3-O-[(3RS)-3-nonylnonadecanoyl]-2-{(3R)-3-[2-(trimethylsilyl) ethoxymethoxy]tetradecanamido}-β-D-glucopyranoside The compound 1(400 mg) was reacted with (RS)-3-nonylnonadecanoic acid (the compound 35') (535 mg) in the same manner as that for the compound 2 to give an amorphous compound 4 (650 mg).

[α]$_D$: −11.8° (C=1.0, CH$_2$Cl$_2$)

IR: the same as that for the compound 2

$^1$H—NMR: the same as that for the compound 2 with the exception of —CH$_2$— integration value Compound 5

2-(trimethylsilyl)ethyl 2-deoxy-4,6-O-isopropyriden-3-O-[(3RS)-3-nonylheneicosanoyl]-2-{(3R)-3-[2-(trimethylsilyl)ethoxymethoxy]tetradecanamido}-β-D-glucopyranoside The compound 1 (400 mg) was reacted with (RS)-3-nonylheneicosanoic acid (the compound 36') (568 mg) in the same manner as that for the compound 2 to furnish an amorphous compound 5 (670 mg). Physical data of this product were as follows:

[α]$_D$: −12.1° (C=0.93,)

IR: the same as that for the compound 2

1H—NMR: the same as that for the compound 2 except for a —CH$_2$— integration value Compound 6

2-(trimehylsilyl)ethyl 2-deoxy-4,6-O-isopropyriden-2-{(3R)-3-[2-(trimethylsilyl)ethoxymethoxy]tetradecanamido}-3-O-[(3RS)-3-undecylpentadecanoyl]-β-D-glucopyranoside The compound 1 (400 mg) was reacted with (RS)-3-undecylpentadecanoic acid (the compound 37') (353 mg) in the same manner as that for the compound 2 to yield an amorphous compound 6 (520 mg). Physical data of this product were as follows:

[α]$_D$: −9.8° (C=1.02, CH$_2$Cl$_2$)

IR : the same as that for the compound 2

$^1$H—NMR: the same as that for the compound 2 except for a —CH$_2$— integration value Compound 7

2-(trimethylsilyl)ethyl 2-deoxy-4,6-O-isopropyriden-2-{(3R)-3-[2-(trimethylsilyl)ethoxymethoxy[tetradecanamido}-3-O-[(3RS)-3-undecylheptadecanoyl]-β-D-glucopyranoside The compound 1 (400 mg) was treated with (RS)-3 undecylheptadecanoic acid (the compound 38′) (375 mg) in the same manner as that for the compound 2 to give an amorphous compound 7 (400 mg). Physical data of this product were as follows:

[α]$_D$: −12.4° (C=1.21, CH$_2$Cl$_2$)
IR: the same as that for the compound 2
$^1$H—NMR: the same as that for the compound 2 except for a —CH$_2$— integration value

Compound 8

2-(trimethylsilyl)ethyl 2-deoxy-4,6-O-isopropyriden-2-{(3R)-3-[2-(trimethylsilyl)-ethoxymethoxy]tetradecanamido}-3-O-[(3RS)-3-undecylnonadecanoyl]-β-D-glucopyranoside The compound 1 (400 mg) was reacted with (RS)-3-undecylnonadecanoic acid (the compound 39′) (400 mg) in the same manner as that for the compound 2 to afford an amorphous compound 8 (480 mg). Physical data of this product were as follows:

[α]$_D$: −11.8° (C=0.88, CH$_2$Cl$_2$)
IR : the same as that for the compound 2
$^1$H—NMR: the same as that for the compound 2 except for a —CH$_2$— integration value

Compound 9

2-(trimethylsilyl)ethyl 2-deoxy-4,6-O-isopropyriden-2-{(3R)-3-[2-(trimethylsilyl)-ethoxymethoxy]tetradecanamido}-3-O-[(3RS)-3-undecylheneicosanoyl]-β-D-glucopyranoside The compound 1 (400 mg) was reacted with (RS)-3-undecylheneicosanoic acid (the compound 40′) (425 mg) in the same way as that for the compound 2 to furnish an amorphous compound 9 (990 mg). This product showed the following physical data:

[α]$_D$: −12.3° (C=1.07, CH$_2$Cl$_2$)
IR : the same as that for the compound 2
$^1$H—NMR: the same as that for the compound 2 except for a —CH$_2$— integration value Production Example II-3(The Third Step; Production of the Compound [v])

Compound 15*

1,5-anhydro-2-deoxy-2-{(3R)-3-[2-(trimethylsilyl) ethoxymethoxy] tetradecanamido}-3-0-[(3RS)-3-undecylheptadecanoyl]-D-glucitol The compound 7* (2.7 g) was dissolved into 95% aqueous acetic acid (60 ml), and the solution was stirred at 50° C. for five hours. Toluene was added to the reaction solution, and the solvent was removed under a reduced pressure. The residue was purified by a silica gel column (n-hexan/ethyl acetate=2/1 to 1/1) to yield an amorphous compound 15 (1.84 g, yield: 91%). Physical data of this product were as follows:

IR (film) cm$^{-1}$: 3600–3100, 2900, 1720, 1650, 1540, 1463, 1380
$^1$H—NMR (300 MHz, CDCl$_3$) δ: 0.02 (s, 9H, Me$_3$Si), 0.85–0.96 (m, 11H, TSMCH$_2$, —Me), 1.10–1.65 (m, 66H, —CH$_2$—), 1.85 (m, 1H, —CH<), 2.65 (brs, 1H, —OH), 3.13 (t, 1H, J=10 Hz, H-1), 3.32 (m, 1H, H-5), 3.52–3.95 (m, 6H, H-1, —CH$_2$—CH$_2$TMS, H-4, H$_2$-6), 4.0–4.17 (m, 2H, H-2, —CH—OSEM), 4.63, 4.69 (AB, 2H, J=7 Hz, —OCH$_2$O—), 4.85 (t, 1H, J=9.4 Hz, H-3), 6.29 (d, 1H, J=7.3 Hz, NH)

Compound 10

2-(trimethylsilyl)ethyl 2-deoxy-3-O-[(3RS)-3-nonylpentadecanoyl]-2-{(3R)-3-[2-(trimethylsilyl)ethoxymethoxy]tetradecanamido}-β-D-glucopyranoside The compound 2 (570 mg) was dissolved in 80% aqueous acetic acid (100 ml). After stirring at 50° C. for two hours, the solution was concentrated, and the residue was subjected to a column chromatography. Elution with CH$_2$Cl$_2$/MeOH=200/1 afforded a syrupy compound 10 (430 mg, yield: 78.4%). Physical data of this product were as follows:

[α]$_D$: −1.6° (C=0.77, CH$_2$Cl$_2$)
IR (film)cm$^{-1}$: 3300, 2930, 2860, 1760, 1650, 1550, 860, 840
$^1$H—NMR (270 MHz, CDCl$_3$) δ: 0.0 (m, 18H, Me$_3$Si), 0.8–1.0 (m, 13H, TMSCH$_2$, —Me), 1.1–1.7 (m, 59H, —CH$_2$—, —CH—), 2.29 (m, 4H, —COCH$_2$—), 3.10 (brs, 2H, OH), 3.40–4.0 (m, 10H, TMSCH$_2$CH$_2$, H-3 of C$_{14}$-OSEM, H-2,4,5,6), 4.6–4.75 (m, 3H, —OCH$_2$O—, H-1), 5.13 (t, 1H, J=9.2 Hz, H-3), 6.32 (d, 1H, J=8.1 Hz, NH)

In the same manner as described above, the following amorphous compounds 11–17 were prepared from the compounds 3–9. The yields were 80–90%, respectively.

Compound 11

2-(trimethylsilyl)ethyl 2-deoxy-3-0-[(3RS)-3-nonylheptadecanoyl]-2-{(3R)-3-[2-(trimethylsilyl)ethoxymethoxy]tetradecanamido}-β-D-glucopyranoside

Compound 12

2-(trimethylsilyl)ethyl 2-deoxy-3-0-[(3RS)-3-nonylnonadecanoyl]-2-{(3R)-3-[2-(trimethylsilyl)ethoxymethoxy]tetradecanamido}-β-D-glucopyranoside

Compound 13

2-(trimethylsilyl)ethyl 2-deoxy-3-0-[(3RS)-3-nonylheneicosanoyl]-2-{(3R)-3-[2-(trimethylsilyl)ethoxymethoxy]tetradecanamido}-β-D-glucopyranoside

Compound 14

2-(trimethylsilyl)ethyl 2-deoxy-2-{(3R)-3-[2-(trimethylsilyl)ethoxymethoxy]tetradecanamido}-3-0-[(3RS)-3-undecylpentadecanoyl]-β-D-glucopyranoside

Compound 15

2-(trimethylsilyl)ethyl 2-deoxy-2-{(3R)-3-[2-(trimethylsilyl)ethoxymethoxy]tetradecanamido}-3-O-[(3RS)-3-undecylheptadecanoyl]-β-D-glucopyranoside

Compound 16

2-(trimethylsilyl)ethyl 2-deoxy-2-{(3R)-3-[2-(trimethylsilyl)ethoxymethoxy]tetradecanamido}-3-O-[(3RS)-3-undecylnonadecanoyl]-β-D-glucopyranoside

Compound 17

2-(trimethylsilyl)ethyl 2-deoxy-2-{(3R)-3-[2-(trimethylsilyl)ethoxymethoxy]tetradecanamide}-3-O-[(3RS)-3-undecylheneicosanoyl]-β-D-glucopyranoside The compounds 11–17 showed the following physical data:

the compound 11
[β]$_D$: −1.6° (C=0.73, CH$_2$Cl$_2$),
the compound 12
[β]$_D$: −1.4° (C=0.99, CH$_2$Cl$_2$),
the compound 13
[β]$_D$: −1.6° (C=1.00, CH$_2$Cl$_2$),
the compound 14
[β]$_D$: −4.2° (C=0.48, CH$_2$Cl$_2$), the compound 15
[β]$_D$: −3.1° (C=0.58, CH$_2$Cl$_2$),
the compound 16
[β]$_D$: −2.9° (C=0.56, CH$_2$Cl$_2$),
the compound 17
[β]$_D$: −2.4° (C=0.42, CH$_2$Cl$_2$)

The IR and $^1$H—NMR of these compounds were the same as those for the compound 10 except for a —CH$_2$— integration value.

Production Example II-4 (The Fourth Step; Production of the Compound [VI])

Compound 23*

1,5-anhydro-6-O-(tert)-butyldiphenylsilyl-2-deoxy-2-{(3R)-3-[2-(trimethylsilyl)ethoxymethoxy]tetradecanamido}-3-O-[(3RS)-3-undecylheptadecanoyl]-D-glucitol To a solution (10 ml) of the compound 15* (1.0 g) and imidazol (220 mg) in dimethylformamide (10 ml) was dropwise added tert-butyldiphenylsilyl chloride (0.42 ml) with stirring under ice-cooling. Three hours later, the reaction solution was diluted with chloroform, and washed with water. The organic layer was dried with anhydrous MgSO$_4$, and concentrated under a reduced pressure. The residue was purified by a silica gel column (CH$_2$Cl$_2$/MeOH=100/1) to afford an oily compound 23* (1.17 g, yield: 93%). Physical data of this product were as follows:

IR(film)cm$^{-1}$: 3600–3200, 2940, 2880, 1725, 1650, 1550, 1470, 1380, 860, 705

$^1$H—NMR(300 MHz, CDCl$_3$) δ: 0.02(s, 9H, Me$_3$Si), 0.85–0.96 (m, 11H, TMSCH$_2$, —Me), 1.05 (s, 9H, —C-Me$_3$), 1.15–1.60 (m, 66H, —CH$_2$—), 1.85 (m, 1H, —CH<), 2.20-2 45 (m, 4H, —COCH$_2$), 2.94 (d, 1H, J=2.8 Hz, —OH), 3.04 (t, 1H, J=9.8 Hz, H-1), 3.32 (m, 1H, H-5), 3.50–4.00 (m, 6H, H-1, —OCH$_2$CH$_2$TMS,H-4, H$_2$-6), 4.00–4.18 (m, 2H, H-2, —CHOSEM), 4 66, 4.68 (AB, 2H, J$_{AB}$=6.9 Hz, —OCH$_2$O—), 4.86 (t, 1H, J=9.2 Hz, H-3), 6.20 (d, 1H, J=6.9 Hz, NH), 7.42 (t, 6H, J=7.2 Hz, Ph(m—,p—)), 7.67 (d, 4H, J=7.2 Hz, Ph(o—))

Compound 18

2-(trimethylsilyl)ethyl 6-O-(tert)butyldimethylsilyl-2-deoxy-3-O-[(3RS)-3-nonylpentadecanoyl]-2-{(3R)-3-[2-(trimethylsilyl)ethoxymethoxy]tetradecanamido}-β-D-glucopyranoside To a solution of the compound 10 (390 mg) in pyridine (10 ml) was added tert-butyldimethylsilyl chloride (116 mg) under ice-cooling. After stirring at room temperature overnight, the methanol was added and the mixture was concentrated under a reduced pressure. The residue was subjected to a column chromatography. Elution with CH$_2$Cl$_2$/MeOH=300/1 afforded an amorphous compound 18 (420 mg). Physical data of this product were as follows:

[α]$_D$: −7.3° (C=1.18, CH$_2$Cl$_2$)

IR(film)cm$^{-1}$: 3500, 33,00, 2930, 2850, 1730, 1640, 1550, 860, 830

$^1$H—NMR(270 MHz, CDCl$_3$) δ: 0.0 (m, 24H, Me$_3$Si), 0.8–1.0 (m, 22H, TMSCH$_2$, Si-(tert)-Bu, -Me), 1.1–1.65 (m, 59H, —CH$_2$—, —CH—), 2.2–2.45 (m, 4H, —COCH$_2$—), 3.2 (d, 1H, J=2.6 Hz, OH), 3.35–4.00 (m, 10H, TMSCH$_2$CH$_2$, H-3 of C$_{14}$-OSEM, H-2, 4, 5, 6) 4.53 (d, 1H, J=8.4 Hz, H-1), 4.66 (2d, 2H, J=6.8 Hz, —OCH$_2$O—), 5.10 (t, 1H, J=9 2 Hz, H-3), 6.13 (d, 1H, J=8.8 Hz, NH)

In the same way as described above, the following amorphous compounds 19–25 were perpared from the compounds 11–17. The yields were 80–90%, respectively.

Compound 19

2-(trimethylsilyl)ethyl 6-O-(tert)butyldimethylsilyl-2-deoxy-3-O-[(3RS)-3-nonylheptadecanoyl]-2-{(3R)-3-[2-(trimethylsilyl)ethoxymethoxy]tetradecanamido}-β-D-glucopyranoside Compound 20

2-(trimethylsilyl)ethyl 6-O-(tert)butyldimethylsilyl-2-deoxy-3-O-[(3RS)-3-nonylnonadecanoyl]-2-{(3R)-3-[2-(trimethylsilyl)ethoxymethoxy]tetradecanamido}-β-D-glucopyranoside Compound 21

2-(trimethylsilyl)ethyl 6-O-(tert)butyldimethylsilyl-2-deoxy-3-O-[(3RS)-3-nonylheneicosanoyl]-2-{[3R)-3-[2-(trimethylsilyl)ethoxymethoxy]tetradecanamido}-β-D-glucopyranoside Compound 22

2-(trimethylsilyl)ethyl 6-O-(tert)butyldimethylsilyl-2-deoxy-2-{(3R)-3-[2-(trimethylsilyl)ethoxymethoxy]tetradecanamido}-3-O-[(3RS)-3-undecylpentadecanoyl]-β-D-glucopyranoside Compound 23

2-(trimethylsilyl)ethyl 6-O-(tert)butyldimethylsilyl-2-deoxy-2-{(3R)-3-[2-(trimethylsilyl)ethoxymethoxy]tetradecanamido)-3-O-[(3RS)-3-undecylheptadecanoyl]-β-D-glucopyranoside Compound 24

2-(trimethylsilyl)ethyl 6-O-(tert)butyldiemthylsilyl-2-deoxy-2-{(3R)-3-[2-(trimethylsilyl)ethoxymethoxy]tetradecanamido)-3-O-[(3RS)-3-undecylnonadecanoyl]-β-D-glucopyranoside Compound 25

2-(trimethylsilyl)ethyl 6-O-(tert)butyldimethylsilyl-2-deoxy-2-{(3R)-3-[2-(trimethylsilyl)ethoxymethoxy]tetradecanamido)-3-O-[(3RS)-3-undecylheneicosanoyl]-β-D-glucopyranoside Physical data of the compounds 19–25 are as follows:
The compound 19
[α]$_D$: −6.8° (C=1.12, CH$_2$Cl$_2$)
The compound 20
[α]$_D$: −7.0° (C=1.37, CH$_2$Cl$_2$)
The compound 21
[α]$_D$: 7.5° (C=0.69, CH$_2$Cl$_2$)
The compound 22
[α]$_D$: −7.1° (C=1.15, CH$_2$Cl$_2$)
The compound 23
[α]$_D$: −7.2° (C=0.72, CH$_2$Cl$_2$)
The compound 24
[α]$_D$: −6.6° (C=0.75, CH$_2$Cl$_2$)
The compound 25
[α]$_D$: −6.6° (C=0.66, CH$_2$Cl$_2$)

The IR and $^1$H—NMR were the same as those for the compound 18 except for a —CH$_2$— integration value.

Production Example II-5 (The Fifth Step; Production of the Compound [VIII])

Compound 31*

1,5-anhydro-6-O-(tert)-butyldiphenylsilyl-2-deoxy-4-O-diphenylphosphono-2-{(3R)-3-[2-(trimethylsilyl)ethoxymethoxy]tetradecanamido}-3-O-[(3RS)-3-undecylheptadecanoyl]-D-glucitol The compound 23* (1.0 g) and DMAP (0.21 g) were dissolved in a mixture of dichloromethane (2 ml) and pyridine (1 ml). To the solution, diphenyl phosphochloridate (0.6 ml) was added dropwise in an argon atmosphere under ice-cooling. After stirring for three hours, the reaction solution was diluted with chloroform, washed with water, dried and concentrated. The obtained residue was purified by a silica gel column (n-hexan/ethyl acetate=8/1) to give an oily compound 31* (1.08 g, yield: 91%).

IR(film)cm$^{-1}$: 3380, 3320, 2936, 2860, 1745, 1685, 1590, 1470, 1380, 1190, 955, 705, 690

$^1$H—NMR (300 MHz, CDCl$_3$) δ: 0.04 (s, 9H, Me$_3$-Si—), 0.86-0.98 (m, 11H, TMSCH$_2$, —Me), 1.03 (s, 9H, —CMe$_3$), 1.13-1.65 (m, 66H, —CH$_2$—), 1.70 (m, 1H, —CH<), 2.10-2.40 (m, 4H, —COCH$_2$—), 3.09 (t, 1H, J=10.7 Hz, H-1), 3.44-4.00 (m, 6H, H-1, H-5, H$_2$-6, —OCH$_2$CH$_2$TMS), 4.10-4.28 (m, 2H, H-2, —CHOSEM), 4 69 (s, 2H, —OCH$_2$O—), 4.88 (q, 1H, J=9.2 Hz, H-4), 5.16 (t, 1H, J=9.3 Hz, H-3), 6.19 (d, 1H, J=7.0 Hz, NH), 7.02-7 70 (m, 20H, —Ph)

Compound 26

2-(trimethylsilyl)ethyl 6-O-(tert)butyldimethylsilyl-2-deoxy-4-0-diphenylphosphono-3-O-[(3RS)-3-nonylpentadecanoyl]-2-{(3R)-3-[2-(trimethylsilyl)ethoxymethoxy]tetradecanamido}-β-D-glucopyranoside The compound 18 (360 mg) and DMAP (78 mg) were dissolved in a mixture of pyridine (5 ml) and CH$_2$Cl$_2$ (2 ml). To this solution, diphenyl phosphorochloridate (171 mg) was added under ice-cooling, and the mixture was stirred at room temperature overnight. Then methanol was added in order to decompose an excess reagent, followed by concentration under a reduced pressure. The residue was extracted with dichloromethane, and the organic layer was washed successively with 2N-hydrochloric acid and water and dried over Na$_2$SO$_4$. After removing the solvent, the residue was purified by a column chromatography (CH$_2$Cl$_2$/MeOH=200/1) to afford a syrupy compound 26 (260 mg, yield: 60%).

IR (film)cm$^{-1}$: 3300, 2930, 2850, 1740, 1660, 1540, 950, 860, 830, 770-680

$^1$H—NMR(270 MHz, CDCl$_3$) δ: 0.0 (m, 24H, Me$_3$-Si—), 0.8-1.0 (m, 22H, TMSCH$_2$, Si-(tert)-Bu, —Me), 1.0-1.6 (m, 59H, —CH$_2$—, —CH—), 2.1-2.4 (m, 4H, —COCH$_2$—), 3.45-3.95 (m, 9H, TMSCH$_2$CH$_2$, H-3, of C$_{14}$-OSEM, H-2,5,6), 4.55-4.8 (m, 4H, —OCH$_2$O—, H-1,4), 5.46 (t, 1H, J=9.2 Hz, H-3), 6.10 (d, 1H, J=8.8 Hz, NH), 7.1-7.4 (m, 10H, Ph)

In the same way as described above, the following syrup-like compounds 27-33 were prepared from the compounds 19-25. The yields were 60-80%, respectively.

Compound 27

2-(trimehtylsilyl)ethyl 6-O-(tert)butyldimethylsilyl-2-deoxy-4-0-diphenylphosphono-3-O-[(3RS)-3-nonylheptadecanoyl]-2-{(3R)-3-[2-(trimethylsilyl)ethoxymethoxy]tetradecanamido)-β-D-glucopyranoside

Compound 28

2-(trimethylsilyl)ethyl 6-O-(tert)butyldiemthylsilyl-2-deoxy-4-O-diphenylphosphono-3-O-[(3RS)-3-nonylnonadecanoyl]-2-{(3R)-3-[2-trimethylsilyl)ethoxymethoxy]tetradecanamido}-β-D-glucopyranoside

Compound 29

2-(trimethylsilyl)ethyl 6-O-(tert)butyldimethylsilyl-2-deoxy-4-O-diphenylphosphono-3-O-[(3-nonylheneicosanoyl]-2-{(3R)3-[2-(trimethylsilyl)ethoxymethoxy]tetradecanamido}-β-D-glucopyranoside

Compound 30

2-(trimethylsilyl)ethyl 6-O-(tert)butyldimethylsilyl-2-deoxy-4-O-diphenylphosphono-2-{(3R)-3-[2-(trimethylsilyl)ethoxymethoxy]tetradecanamido}-3-O-[(3RS)-3-undecylpentadecanoyl]-β-D-glucopyranoside

Compound 31

2-(trimethylsilyl)ethyl 6-O-(tert)butyldimethylsilyl-2-deoxy-4-O-diphenylphosphono-2-}(3R)-3-[2-(trimethylsilyl)ethoxymethoxy]tetradecanamido)-3-O-[(3RS)-3-undecylheptadecanoyl]-β-D-glucopyranoside

Compound 32

2-(trimethylsilyl)ethyl 6-O-(tert)butyldimethylsilyl-2-deoxy-4-O-diphenylphosphono-2-}(3R)-3-[2-(trimethylsilyl)ethoxymethoxy]tetradecanamido}-3-O-[(3RS)-3-undecylnonadecanoyl]-β-D-glucopyranoside

Compound 33

2-(trimehylsilyl)ethyl 6-O-(tert)butyldimethylsilyl-2-deoxy-4-O-diphenylphosphono-2-{(3R)-3-[2-(trimethylsilyl)ethoxymethoxy]tetradecanamido}-3-O-[(3RS)-3-undecylheneicosanoyl]-β-D-glucopyranoside Physical data of the compounds 27-33 are as follows:

The compound 27
[α]$_D$: +1.6° (C=0.74, CH$_2$Cl$_2$)

The compound 28
[α]$_D$: +1.7° (C=0.80, CH$_2$Cl$_2$)

The compound 29
[α]$_D$: +1.8° (C=0.74, CH$_2$Cl$_2$)

The compound 30
[α]$_D$: +2.0° (C=0.88, CH$_2$Cl$_2$)

The compound 31
[α]$_D$: +1.5° (C=0.95, CH$_2$Cl$_2$)

The compound 32
[α]$_D$: +1.4° (C=1.02, CH$_2$Cl$_2$)

The compound 33
[α]$_D$: +3.0° (C=0.67, CH$_2$Cl$_2$)

The IR and $^1$H—NMR of these compounds were the same as those for the compound 26, except for a —CH$_2$— integration value.

Production Example II-6 (The Sixth Step; Production of the Compound [VIII])

Compound 39*

1.5-anhydro-2-deoxy-4-O-diphenylphosphono-2-[(3R)-3-hydroxytetradecanamido]-3-O-[(3RS)-3-undecylheptadecanoyl]-D-glucitol To a stirred solution of the compound 31* (1.0 g) in dichloromethane (20 ml) was dropwise added BF$_3$.O-

Et$_2$ (1 ml) under ice-cooling. One hour later, the reaction solution was further stirred at room temperature overnight. The solution was diluted with chloroform, washed with water and sodium bicarbonate, and dried with anhydrous MgSO$_4$. Then, the solvent was removed under a reduced pressure, and the residue was purified by a silica gel column (CHCl$_3$/MeOH = 100/1) to furnish an amorphous compound 39* (470 mg, yield: 64%). Physical data of this product were as follows:

IR(KBr) cm$^{-1}$: 3600–3200, 2920, 2850, 1740, 1655, 1590, 1490, 1467, 1285, 1190, 1020, 955, 770, 720, 690

$^1$H—NMR (300 MHz, CDCl$_3$) δ: 0.88 (t, 9H, J=6.2 Hz, —Me), 1.0–1.6 (m, 66H, —CH$_2$—), 1.72–1.82 (m, 1H, —C$\underline{H}$<), 2.04–2.42 (m, 4H, —COCH$_2$—), 3.14–3.18 (m, 2H, 6-OH, H-1), 3.22 (m, 1H, H-1), 3.34 (1H, brd, J=9.3 Hz, H-5), 3.42–3.78 (m, 3H, H$_2$-6,3'-OH), 3.92 (m, 1H, H-3'), 4.08–4.25 (m, 1H, H-2), 4.76 (q, 1H, J=9.4 Hz, H-4), 5.18 (t, 1H, J=9.5 Hz, H-3), 6.16 (d, 1H, J=7.1 Hz, NH), 7.14–7.38 (m, 10H, Ph)

Compound 34

2-deoxy-4-O-diphenylphosphono-2-[(3R)-3-hydroxytetradecanamido]-3-0-[(3RS)-3-nonylpentadecanoyl]-D-glucopyranose To a solution of the compound 26 (190 mg) in dichloromethane (10 ml) was added BF$_3$.OEt$_2$ (0.5 ml) under ice-colling, and the solution was stirred at room temperature for two hours. The reaction solution was successively washed with 1M Na$_2$CO$_3$ and water, dried with Na$_2$SO$_4$, and concentrated under a reduced pressure. The residue was subjected to a column chromatography. Elution with CH$_2$Cl$_2$/MeOH = 45/1 gave compound 34 (106 mg, yield: 75%). This compound was suspended in 1.4-dioxane and lyophilized. Physical data of this product were as follows:

mp: 95°–97° C.

[α]$_D$: +1.0° (C=0.99, CH$_2$Cl$_2$)

IR (KBr)cm$^{-1}$: 3350, 2930, 2860, 1740, 1640, 1540, 960, 780–680

$^1$H—NMR (270 MHz, CDCl$_3$) δ: 0.88 (t, 9H, -Me), 1.0–1.8 (m, 59H, —CH$_2$—, —CH—), 2.05–2.35 (m, 4H, —COCH$_2$—), 3.5–4.1 (m, 7H, OH, H-3 of C$_{14}$OSEM, H-5,6), 4.22 (m, 1H, H-2), 4.72 (q, 1H, J=9.5 Hz, H-4), 5.25 (d, 1H, J=3.3 Hz, H-1), 5.50 (t, 1H, J=10.3 Hz, H-3) 6.42 (d, 1H, J=9.3 Hz, NH), 7.1–7.4 (m, 10H, Ph)

In the same manner, following compounds 35–41 were prepared from the compounds 27–33. The yields were 70–80%, respectively.

Compound 35

2-deoxy-4-O-diphenylphosphono-2-[(3R)-3-hydroxytetradecanamido]-3-O-[(3RS)-3-nonylheptadecanoyl]-D-glucopyranose

Compound 36

2-deoxy-4-O-diphenylphosphono-2-[(3R)-3-hydroxytetradecanamido]-3-O-[(3RS)-3-nonylnonadecanoyl]-D-glucopyranose

Compound 37

2-deoxy-4-O-diphenylphosphono-2-[(3R)-3-hydroxytetradecanamido]-3-O-[(3RS)-3-nonylheneicosanoyl]-D-glucopyranose

Compound 38

2-deoxy-4-O-diphenylphosphono-2-[(3R)-3-hydroxytetradecanamido]-3-O-[(3RS)-3-undecylpentadecanoyl]-D-glucopyranose

Compound 39

2-deoxy-4-O-diphenylphosphono-2-[(3R)-3-hydroxytetradecanamido]-3-O-[(3RS)-3-undecylheptadecanoyl]-D-glucopyranose

Compound 40

2-deoxy-4-O-diphenylphosphono-2-[(3R)-3-hydroxytetradecanamido]-3-O-[(3RS)-3-undecylnonadecanoyl]-D-glucopyranose

Compound 41

2-deoxy-4-O-diphenylphosphono-2-[(3R)-3-hydroxytetradecanamido]-3-O-[(3RS)-3-undecylheneicosanoyl]-D-glucopyranose Physical data of the compounds 35–41 are as follows:

The compound 35
mp: 94°–96° C.
[α]$_D$: +1.0° (C=0.12, CH$_2$Cl$_2$)

The compound 36
mp: 96°–98° C.
[α]$_D$: +3.3° (C=0.98, CH$_2$Cl$_2$)

The compound 37
mp: 92°–94° C.
[α]$_D$: +4.9° (C=0.53, CH$_2$Cl$_2$)

The compound 38
mp: 103°–105° C.
[α]$_D$: +1.2° (C=0.99, CH$_2$Cl$_2$)

The compound 39
mp: 101°–103° C.
[α]$_D$: +1.5° (C=0.82, CH$_2$Cl$_2$)

The compound 40
mp: 98°–100° C.
[α]$_D$: +2.2° (C=0.18, CH$_2$Cl$_2$)

The compound 41
mp: 97°–99° C.
[α]$_D$: 0.7° (C=0.61, CH$_2$Cl$_2$)

The IR and $^1$H—NMR of these compounds were the same as those for the compound 34 except for a —CH$_2$— integration value.

Embodiment Example (The Seventh Step: Production of the Compound [I])

Compound 47*

1,5-anhydro-2-deoxy-2-[(3R)-3-hydroxytetradecanamido]-4-0-phosphono-3-0-[(3RS)-3-undecylheptadecanoyl]-D-glucitol The compound 39* (100 gm) was hydrogenated over PtO$_2$ (available from Aldorich, Co.) (80 mg) in a mixture of MeOH/EtOH = 1/1 (30 ml) at room temperature overnight. Then, the catalyst was removed by filtration, and the filterate was concentrated. The residue was suspended in 1,4-dioxane, and lyophilized to give compound 47* as a white powder (66 mg, yield: 77%). Physical data of this product are as follows:

$^1$H—NMR: Signals due to hydrogens in a benzene ring were not present.

mp: 201°–204° C.

IR (KBr)cm$^{-1}$: 3500–3200, 1730, 1655, 1547, 1160, 1102, 1046

Compound 42

2-deoxy-2-[(3R)-3-hydroxytetradecanamido]-3-O-[(3RS)-3-nonylpentadecanoyl]-4-O-phosphono-D-glucopyranose The compound 34 (90 mg) was hydrogenated over PtO$_2$ (100 mg) in EtOH (50 ml) overnight. Then, the catalyst was removed by filtration, and the filerate was concentrated under a reduced pressure, and the residue was lyophilized with 1,4-dioxane to yield a compound 42 (58 mg, yield: 74%). Physical data of this product were as follows:

mp: 163–165° C. (decomp.)
$[\alpha]_D$: +13.3°
(CHCl$_3$/MeOH/water/NH$_4$OH = 50/25/4/2
C = 0.12)
IR(KBr) cm$^{-1}$: 3400, 2930, 2850, 1720, 1640, 1550

In the same manner, the following compounds 43–4 g were prepared from the compounds 35–41. The yields were 70–90%, respectively.

Compound 43

2-deoxy-2-[(3R)-3-hydroxytetradecanamido]-3-O-[(3RS)-3-nonylheptadecanoyl]-4-O-phosphono-D-glucopyranose

Compound 44

2-deoxy-2-[(3R)-3-hydroxytetradecanamido]-3-O-[(3RS)-3-nonylnonadecanoyl]-4-O-phosphono-D-glucopyranose

Compound 45

2-deoxy-2-[(3R)-3-hydroxytetradecanamido]-3-O-[(3RS)-3-nonylheneicosanoyl]-4-O-phosphono-D-glucopyranose

Compound 46

2-deoxy-2-[(3R)-3-hydroxytetradecanamido]-4-O-phosphono-3-O-[(3RS)-3-undecylpentadecanoyl]-D-glucopyranose

Compound 47

2-deoxy-2-[(3R)-3-hydroxytetradecanamido]-4-O-phosphono-3-O-[(3RS)-3-undecylheptadecanoyl]-D-glucopyranose

Compound 48

2-deoxy-2-[(3R)-3-hydroxytetradecanamido]-4-O-phosphono-3-O-[(3RS)-3-undecylnonadecanoyl]-D-glucopyranose

Compound 49

2-deoxy-2-[(3R)-3-hydroxytetradecanamido]-4-O-phosphono-3-O-[(3RS)-3-undecylheneicosanoyl]-D-glucopyranose These compounds 43–49 showed the following physical features:

Compound 43
mp: 161°–163° C. (decomp.)
$[\alpha]_D$: +4.1°
(CHCl$_3$/MeOH/water/NH$_4$OH = 50/25/4/2,
C = 0.64)

Compound 44
mp: 164°–166° C. (decomp.)
$[\alpha]_D$: +5.1°
(CHCl$_3$/MeOH/water/NH$_4$OH = 50/25/4/2,
C = 0.82)

Compound 45
mp: 167°–169° C. (decomp.)
$[\alpha]_D$: +5.0°
(CHCl$_3$/MeOH/water/NH$_4$OH = 50/25/4/2,
C = 0.40)

Compound 46
mp: 157°–160° C. (decomp.)
$[\alpha]_D$: +7.4°
(CHCl$_3$/MeOH/water/NH$_4$OH = 50/25/4/2,
C = 0.41)

Compound 47
mp: 160°–163° C. (decomp.)
$[\alpha]_D$: +9.7°
(CHCl$_3$/MeOH/water/NH$_4$OH = 50/25/4/2,
C = 0.37)

Compound 48
mp: 163°–165° C. (decomp.)
$[\alpha]_D$: +12.5°
(CHCl$_3$/MeOH/water/NH$_4$OH = 50/25/4/2,
C = 0.08)

Compound 49
mp: 166°–168° C. (decomp.)
$[\alpha]_D$: +11.9°
(CHCl$_3$/MeOH/water/NH$_4$OH = 50/25/4/2,
C = 0.27)

We claim:
1. Lipid A monosaccharide analogues of the following formula:

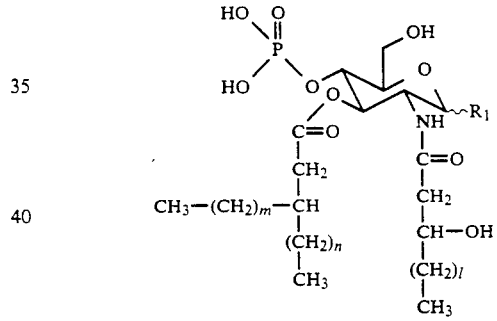

wherein R$_1$ is a hydrogen atom or a hydroxyl group, l is an integer of 8–14, m is an integer of 11–17, and n is an integer of 8–14.

2. Lipid A monosaccharide analogues according to claim 1, wherein R$_1$ is a hydrogen atom.

3. Lipid A monosaccharide analogues according to claim 1, wherein R$_1$ is a hydroxyl group.

4. A pharmaceutical composition comprising a lipid A monosaccharide analogue according to claim 1 and a pharmaceutically acceptable carrier therefor.

5. A pharmaceutical composition comprising of lipid A monosaccharide analogue according to claim 2 and a pharmaceutically acceptable carrier therefor.

6. A pharmaceutical composition comprising a lipid A monosaccharide analogue according to claim 3 and a pharmaceutically acceptable carrier therefor.

* * * * *